United States Patent
Choi et al.

(10) Patent No.: US 9,476,838 B2
(45) Date of Patent: Oct. 25, 2016

(54) HYBRID IMAGING AND SCATTEROMETRY TARGETS

(71) Applicant: KLA-Tencor Corporation, Milpitas, CA (US)

(72) Inventors: DongSub Choi, Gyeonggi-do (KR); Tal Itzkovich, Kfar Uriya (IL); David Tien, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 155 days.

(21) Appl. No.: 14/338,023

(22) Filed: Jul. 22, 2014

(65) Prior Publication Data
US 2014/0375984 A1 Dec. 25, 2014

Related U.S. Application Data

(63) Continuation of application No. PCT/US2014/043267, filed on Jun. 19, 2014.

(60) Provisional application No. 61/837,058, filed on Jun. 19, 2013.

(51) Int. Cl.
| | |
|---|---|
| G01N 21/00 | (2006.01) |
| G01N 21/95 | (2006.01) |
| G01N 21/93 | (2006.01) |
| G01N 21/956 | (2006.01) |
| G03F 7/20 | (2006.01) |

(52) U.S. Cl.
CPC .......... *G01N 21/9501* (2013.01); *G01N 21/93* (2013.01); *G01N 21/956* (2013.01); *G03F 7/70633* (2013.01); *G03F 7/70683* (2013.01)

(58) Field of Classification Search
CPC .. G01N 21/95; G01N 21/65; G01N 15/1459; G01J 3/02; G01J 3/51; G01J 3/513
USPC ...................... 356/300–445, 72–73
See application file for complete search history.

(56) References Cited

U.S. PATENT DOCUMENTS

| | | | |
|---|---|---|---|
| 6,850,811 | B1 | 2/2005 | Stewart |
| 7,879,627 | B2 | 2/2011 | Ghinovker et al. |
| 2003/0223630 | A1 | 12/2003 | Adel et al. |
| 2004/0169861 | A1* | 9/2004 | Mieher ............... G01N 21/956 356/400 |
| 2004/0233441 | A1 | 11/2004 | Mieher et al. |
| 2005/0012928 | A1 | 1/2005 | Sezginer et al. |
| 2009/0262362 | A1 | 10/2009 | de Groot et al. |
| 2011/0043791 | A1* | 2/2011 | Smilde ............... G03F 7/70616 356/128 |

* cited by examiner

*Primary Examiner* — Abdullahi Nur
(74) *Attorney, Agent, or Firm* — Simpson & Simpson, PLLC (57) ABSTRACT

Metrology targets, design files, and design and production methods thereof are provided. The metrology targets are hybrid in that they comprise at least one imaging target structure configured to be measurable by imaging and at least one scatterometry target structure configured to be measurable by scatterometry. Thus, the hybrid targets may be measured by imaging and scatterometry simultaneously or alternatingly and/or the measurement techniques may be optimized with respect to wafer regions and other spatial parameters, as well as with respect to temporal process parameters. The hybrid targets may be used to monitor process parameters, for example via comparative overlay measurements and/or high resolution measurements.

18 Claims, 10 Drawing Sheets

- 210 — INTEGRATING IMAGING AND SCATTEROMETRY TARGET STRUCTURES INTO A SINGLE HYBRID TARGET MEASURABLE BY BOTH IMAGING AND SCATTEROMETRY TECHNIQUES
- 220 — CONFIGURING THE HYBRID TARGETS TO ENABLE SIMULTANEOUS MEASUREMENTS OF ANY OF: IMAGING, ZEROTH ORDER SCOL, FIRST ORDER SCOL, CD-SEM OVERLAY
- 230 — DESIGNING SCOL TARGET STRUCTURES AS SUB-STRUCTURES OF IMAGING TARGET STRUCTURES
- 240 — MODIFYING PITCHES OF PERIODIC STRUCTURES TO BE MEASUREABLE BY BOTH IMAGING AND SCOL TECHNIQUES
- 245 — SEGMENTING THE TARGET STRUCTURES AND MODIFYING PITCHES OF THE SEGMENTATION
- 250 — CARRYING OUT IMAGING AND SCOL MEASUREMENTS SIMULTANEOUSLY
- 260 — USING THE SAME TARGETS, ALTERNATING IMAGING AND SCOL MEASUREMENTS WITH RESPECT TO THE LOCATION OF THE TARGETS OF THE WAFER

HYBRID IMAGING AND SCATTEROMETRY TARGETS

CROSS REFERENCE TO RELATED APPLICATIONS

This application is filed under 35 U.S.C. §120 and §365(c) as a continuation of International Patent Application No. PCT/US2014/043267 filed Jun. 19, 2014, which application claims the benefit of U.S. Provisional Patent Application No. 61/837,058 filed on Jun. 19, 2013, which applications are incorporated herein by reference in their entirety.

BACKGROUND OF THE INVENTION

1. Technical Field

The present invention relates to the field of metrology targets, and more particularly, to metrology targets for combined imaging and scatterometry measurements.

2. Discussion of Related Art

Metrology targets are designed to enable the measurement of parameters that indicate the quality of wafer production steps and quantify the correspondence between design and implementation of structures on the wafer. Imaging metrology targets as specific structures optimize the requirements for device similarity and for optical image measurability and their images provide measurement data. Scatterometry metrology targets on the other hand, yield diffraction patterns at the pupil plane, from which target parameters may be derived.

SUMMARY OF THE INVENTION

One aspect of the present invention provides a metrology target comprising at least one imaging target structure configured to be measurable by imaging and at least one scatterometry target structure configured to be measurable by scatterometry.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Prior to the detailed description being set forth, it may be helpful to set forth definitions of certain terms that will be used hereinafter.

The terms "metrology target" or "target" as used herein in this application, are defined as structures designed or produced on a wafer which are used for metrological purposes. The terms "imaging" and "scatterometry" as used herein in this application, are defined as measurement techniques applied to images (optical or SEM) of target structures at the field plane and to diffraction patterns (of orders zero, one, two etc.) at the pupil plane, respectively. The term "layer" as used herein in this application, is defined as any of the layers used in a photolithography process in any of its steps. The terms "imaging target structures" and "scatterometry target structures" as used herein in this application, are defined as structures designed or produced according to specifications configured to enable imaging or scatterometry metrology measurements, respectively. Target structures may be adapted from any known target designs such as imaging target designs AIM (Advanced Imaging Metrology), BiB (Box-in-Box), AIMid and BLOSSOM and their corresponding variations and alternatives; and scatterometry target designs such as SCOL (Scatterometry Overlay) and their corresponding variations and alternatives. The term "periodic structure" as used in this application refers to any kind of designed or produced structure in at least one layer which exhibits some periodicity. The periodicity is characterized by its pitch, namely its spatial frequency. The term "segmentation" as used in this application refers to any subdivision of an element in a target design to smaller features.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Metrology targets, design files, and design and production methods thereof are provided. The metrology targets are hybrid in that they comprise at least one imaging target structure configured to be measurable by imaging and at least one scatterometry target structure configured to be measurable by scatterometry. Thus, the hybrid targets may be measured by imaging and scatterometry simultaneously or alternatingly and/or the measurement techniques may be optimized with respect to wafer regions and other spatial parameters, as well as with respect to temporal process parameters. The hybrid targets may be used to monitor process parameters, for example via comparative overlay measurements and/or high resolution measurements.

Figure 1A:
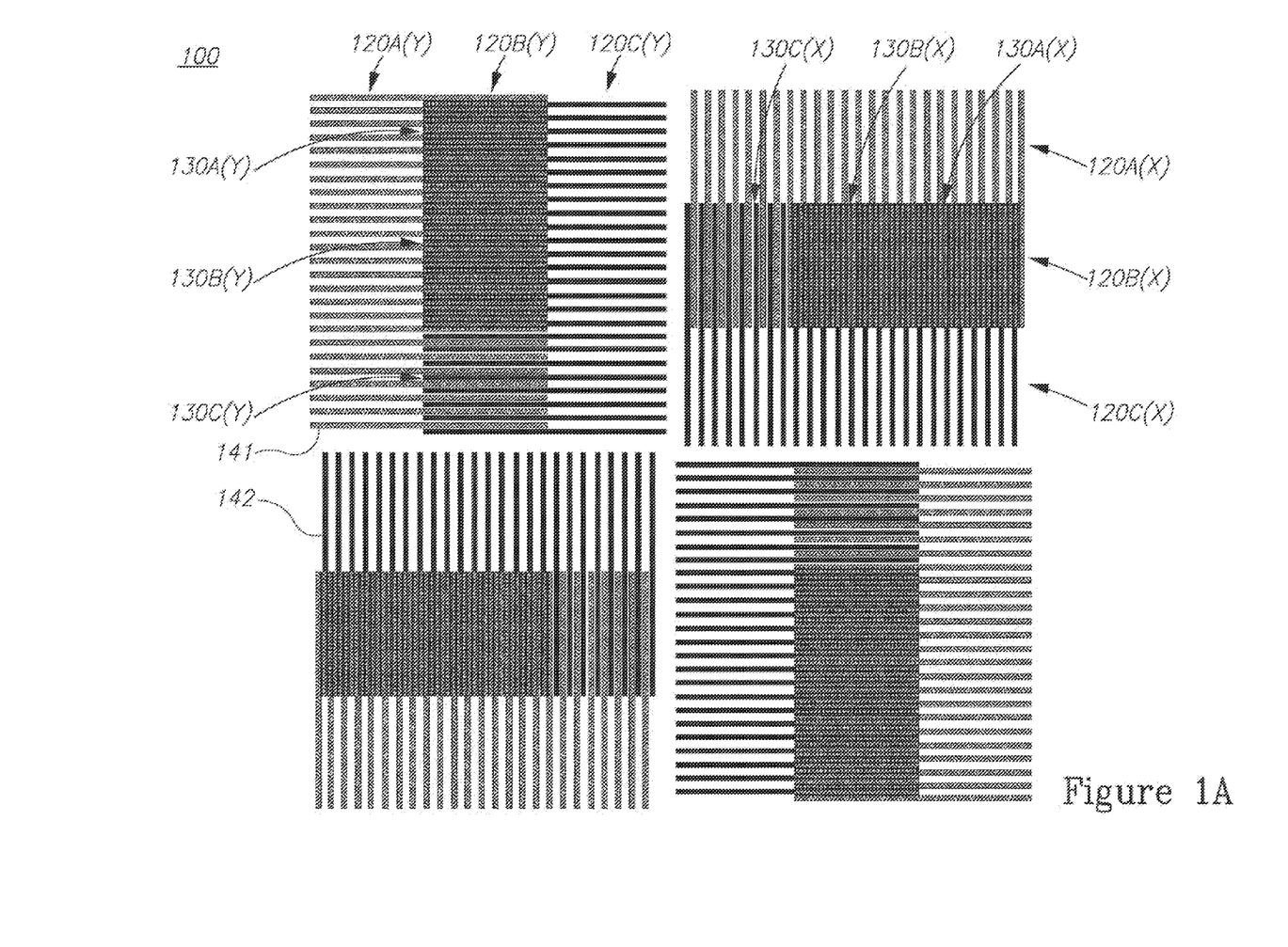
FIGS. 1A and 1B are high level schematic illustrations of hybrid metrology targets, according to some embodiments of the invention.
Figure 1B:
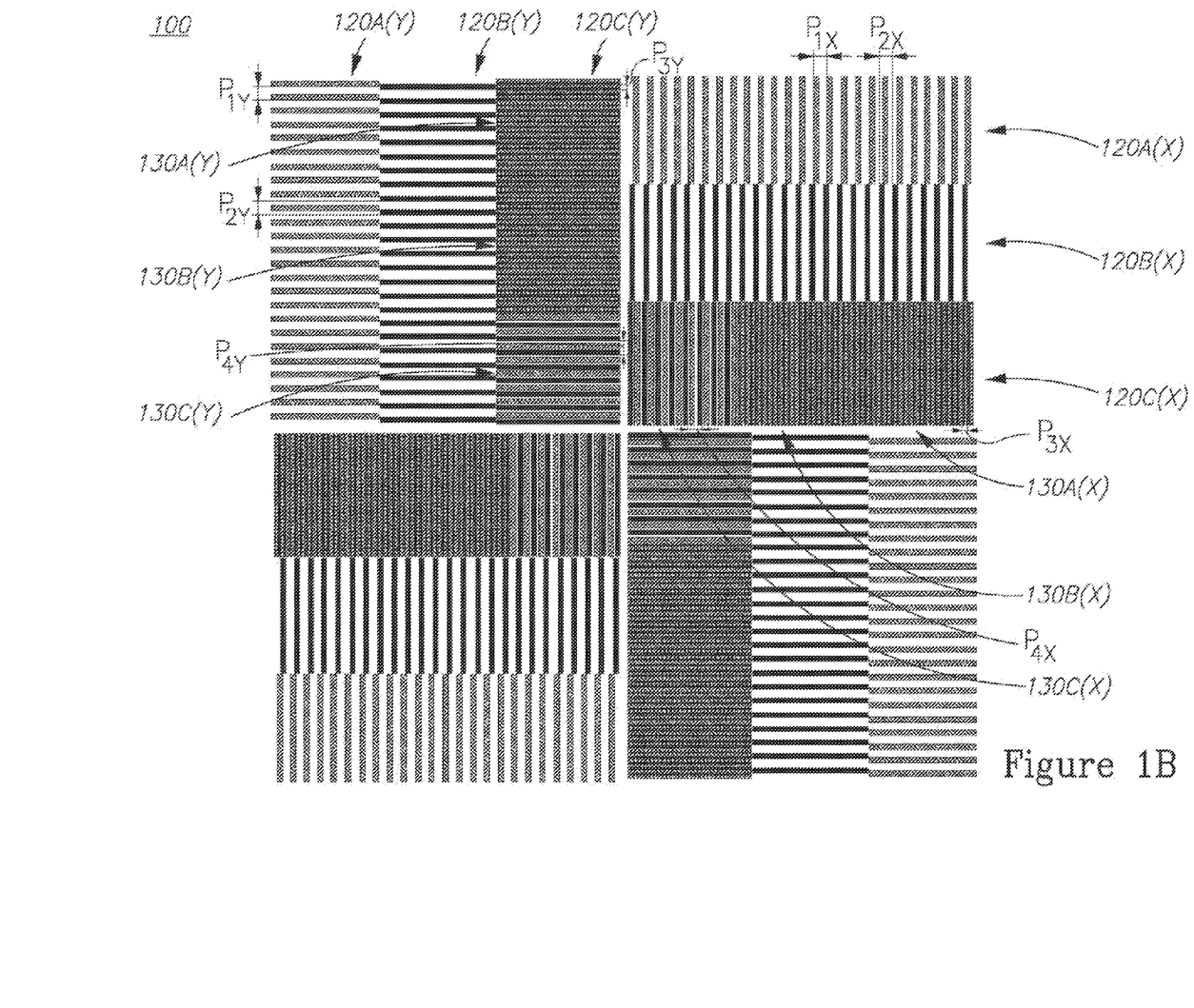

FIGS. 1A and 1B are high level schematic illustrations of hybrid metrology targets 100, according to some embodiments of the invention. Metrology targets 100 integrate imaging and scatterometry overlay (SCOL) target structures into a single hybrid target measurable by both imaging and SCOL techniques Metrology target 100 comprises at least one imaging target structure configured to be measurable by imaging and at least one scatterometry target structure configured to be measurable by scatterometry. For example, FIG. 1A schematically illustrates imaging target structures 120A and 120C as periodic structures, both having X and Y components (i.e., perpendicular substructures which define respective measurement directions) at two respective regions of target 100, and scatterometry target structures 130A, 130B, 130C, which likewise are periodic structures and have X and Y components (i.e., perpendicular substructures which define respective measurement directions) at two respective sub-regions in region 120B of target 100. In the illustrated non-limiting example, imaging target structures 120A and 120C are in two different layers (e.g., structure 120A at an outer previous layer 141 and structure 120C at an inner current layer 142) and have pitches $P_{1X}$, $P_{1Y}$ and $P_{2X}$, $P_{2Y}$ respectively, configured to enable imaging measurements thereof; scatterometry target structures 130A, 130B are grating-over-grating targets with respect to layers 141, 142 and have pitches $P_{3X}$, $P_{3Y}$ configured to yield zeroth order scatterometry measurements; and scatterometry target structures 130C are grating-over-grating targets with respect to layers 141, 142 and have pitches $P_{4X}$, $P_{4Y}$ configured to yield first order scatterometry measurements. In another example, FIG. 1B schematically illustrates target 100 having scatterometry target structures 130A, 130B, 130C switched with imaging target structures 120C with respect to the region of target 100 in which they are located, specifically, in FIG. 1B, imaging target structures 120A, 120B are in the two outer regions while scatterometry target structures 130A, 130B, 130C are at sub-regions of inner region 120C of target 100. The illustrated examples serve illustrative purposes and are not to be understood as limiting the invention. Permutations of regions and of locations of any of target structures 120A-C and 130A-C, as well as addition or removal of imaging and/or scatterometry structures are likewise part of the present disclosure.

Advantageously, targets 100 allow measuring overlay by imaging technology, scatterometry zeroth order technology, and scatterometry first (±1) order technology. Furthermore, targets 100 may also be used for monitoring process parameters such as focus (see details below). Targets 100 thus are more efficient using available space of the wafer and available time for metrology measurements, provide enhanced flexibility in the selection of metrology techniques, provide enhanced accuracy when used for self-referencing (no shift between targets measured by different techniques) and may be measured using dual-mode (imaging and scatterometry) algorithms.

Regions or sub-regions of target 100 may be segmented to enhance compatibility with production process. For example, the segmentation may be designed to restrict or completely avoid continuous target elements line continuous bars or continuous gaps.

Figure 2:
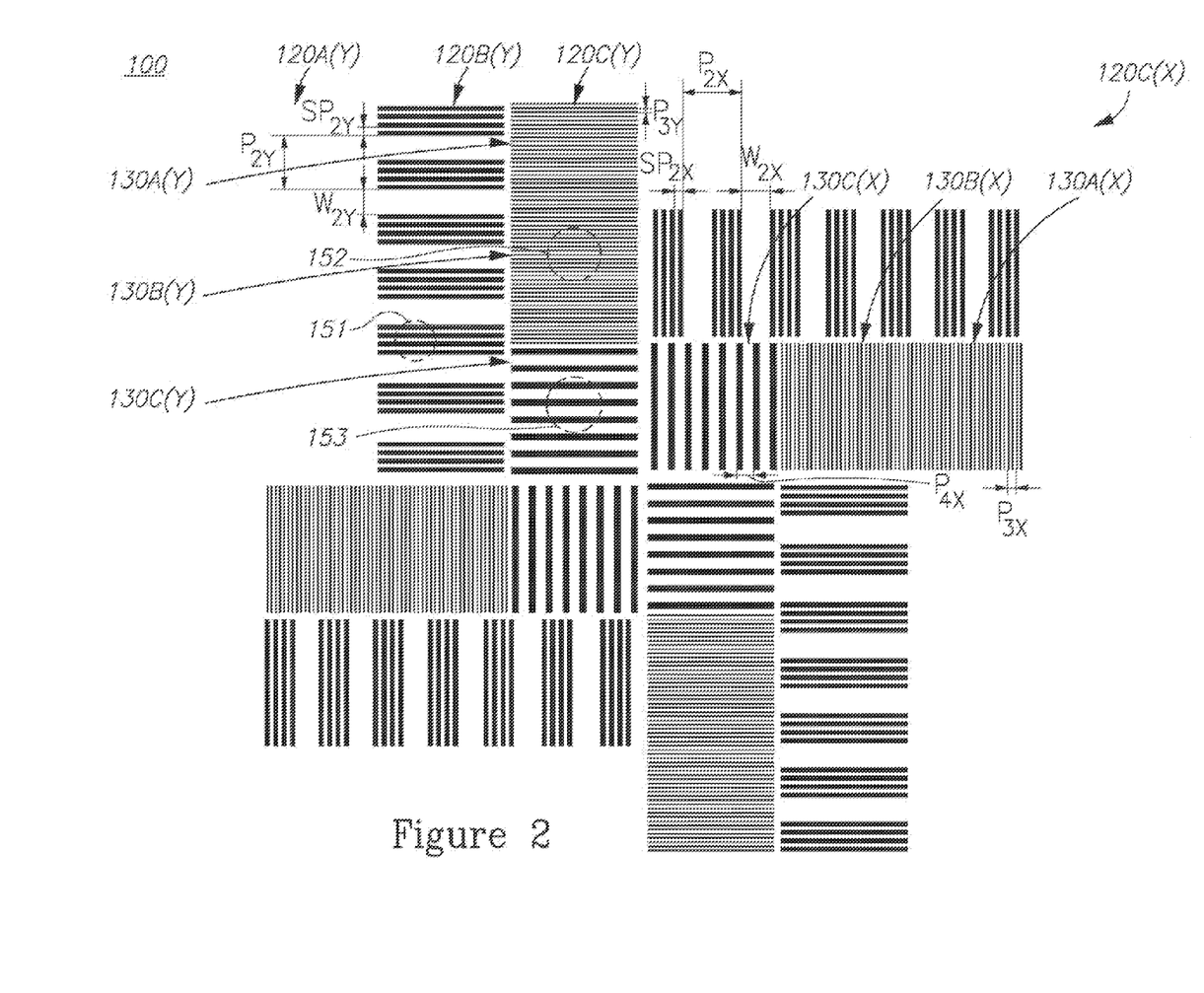
FIG. 2 is a high level schematic illustration of one layer in hybrid metrology targets, according to some embodiments of the invention.

FIG. 2 is a high level schematic illustration of one layer in hybrid metrology targets 100, according to some embodiments of the invention.

For example, FIG. 2 may represent previous layer 141 or current layer 142 in various target designs. For example, FIG. 2 may represent previous layer 141 in a target design which is similar to the one illustrated in FIG. 1B, with layers 141, 142 switched (the inner layer being the previous instead of the current layer, e.g., to enhance robustness with respect to process inaccuracies). As such, segmented bars in regions 120B replace the continuous bars in regions 120B illustrated in FIG. 1B, and may be designed to be more process compatible. Segmentation parameters like segmentation pitch $SP_{2X}$, $SP_{2Y}$ and gaps $W_{2X}$, $W_{2Y}$ between bars as well as pitches $P_{2X}$, $P_{2Y}$ may be adjusted according to process parameters and metrology requirements.

FIG. 2 also illustrates embodiments in which process parameters are monitored, using the different pitches available throughout target 100. For example, ROIs 151, 152, 153, when selected to be small enough, differ in pitch (in the illustrated example, exhibiting pitches $SP_{2Y}$, $P_{3Y}$, $P_{4Y}$ respectively, in a non-limiting example, 2000 nm, 300 nm and 600 nm, see also FIG. 3A below). Process parameters such as focus and dose may be measured, monitored and scaled using the spectrum of pitch values in target 100.

Figure 3A:
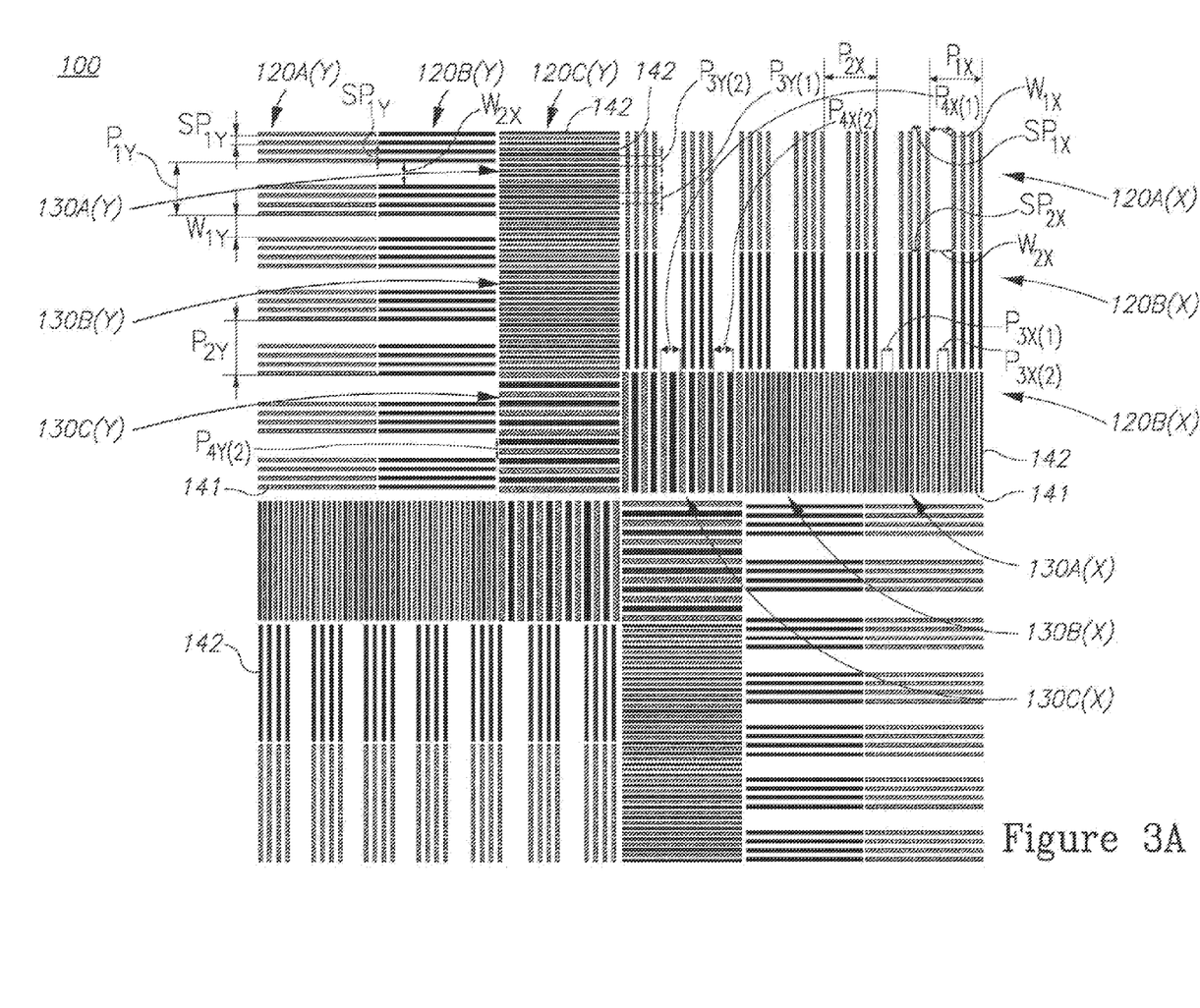
FIGS. 3A-C are high level schematic illustrations of hybrid metrology targets, according to some embodiments of the invention.
Figure 3B:
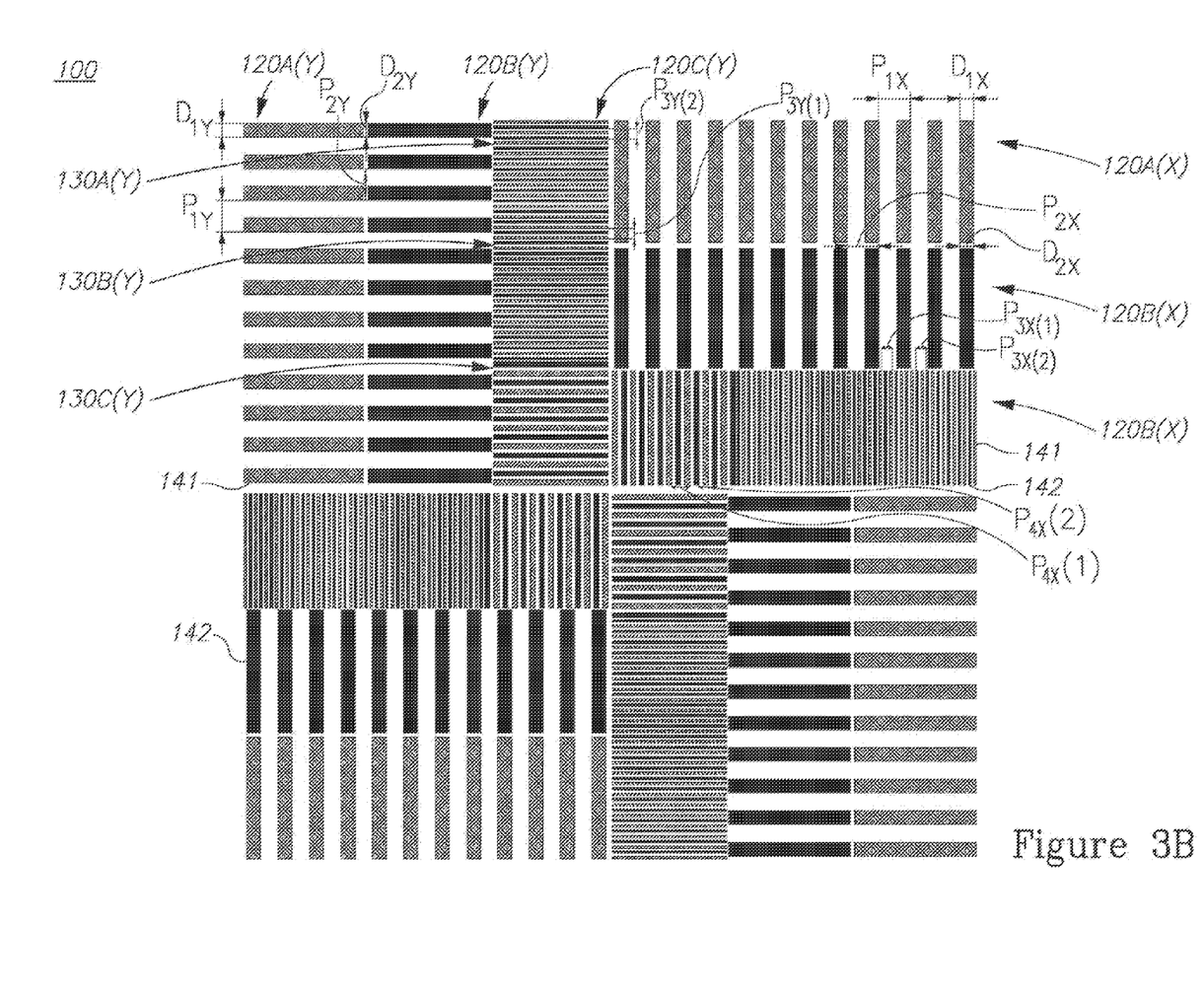
Figure 3C:
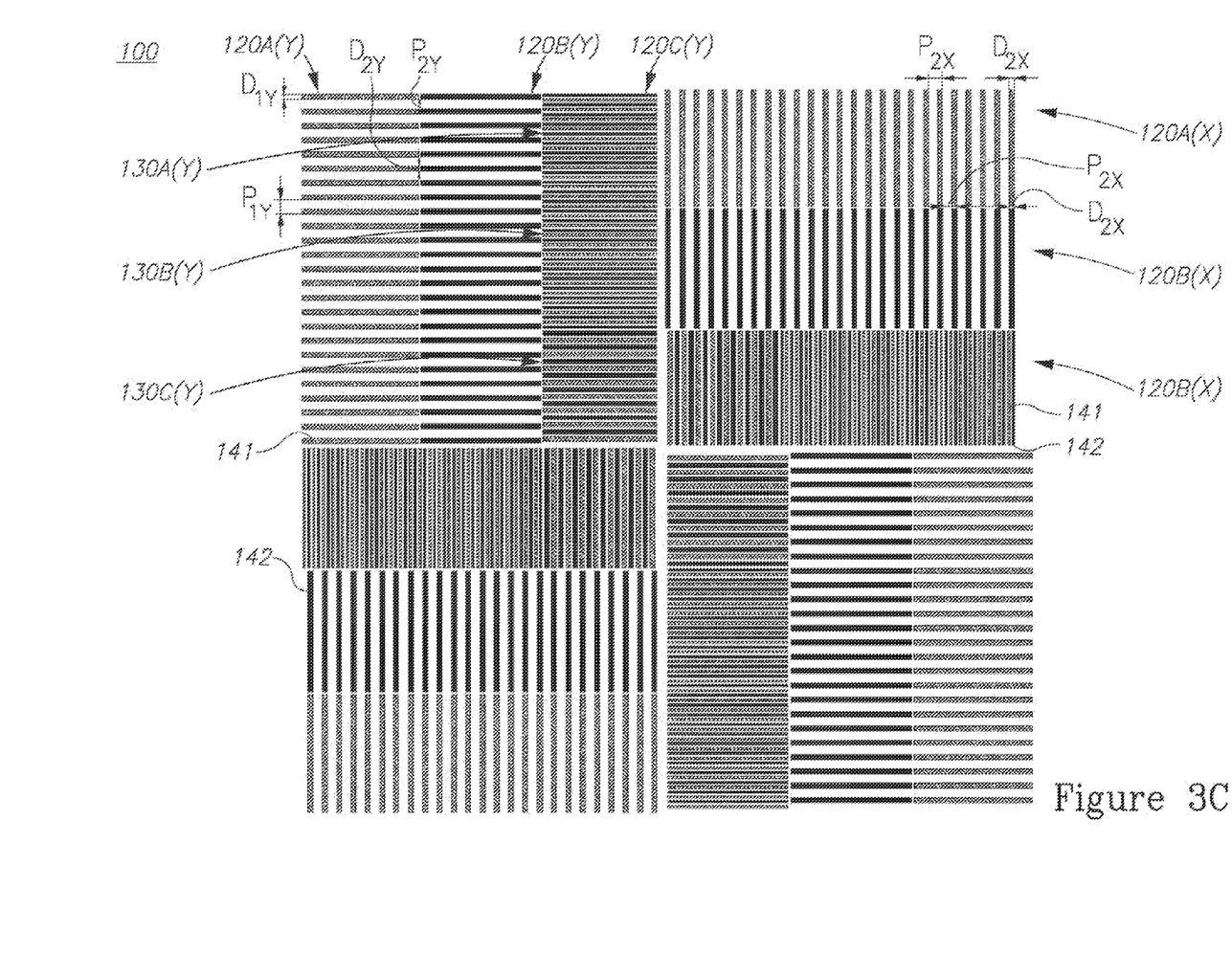

FIGS. 3A-C are high level schematic illustrations of hybrid metrology targets 100, according to some embodiments of the invention. FIGS. 3A-C provide additional non-limiting examples for segmented targets 100 with varying segmentation configurations. As noted above, the present invention discloses any permutation on the ordering of regions 120A-C, 130A-C, additions or removals of target structures, variation of segmentation parameters and application of the disclosed principles to other types of metrology targets and to new designs of metrology targets.

FIG. 3A schematically illustrates target 100 in which imaging target structures 120A and 120B are at layers 141 and 142 respectively and have pitches $P_{1X}$, $P_{1Y}$ and $P_{2X}$, $P_{2Y}$ respectively, segmentation pitches $SP_{1X}$, $SP_{1Y}$ and $SP_{2X}$, $SP_{2Y}$ respectively, and segmentation gaps $W_{1X}$, $W_{1Y}$ and $W_{2X}$, $W_{2Y}$ respectively, configured according to specified requirements; and in which scatterometry target structures 130A,B and 130C have pitches $P_{3X}(1)$, $P_{3Y}(1)$, $P_{3X}(2)$, $P_{3Y}(2)$ and $P_{4X}(1)$, $P_{4Y}(1)$, $P_{4X}(2)$, $P_{4Y}(2)$ respectively, for layers 141 (1) and 142 (2) respectively, configured according to specified requirements. In a non-limiting example, these values may be $P_{1X}=P_{1Y}=P_{2X}=P_{2Y}=2000$ nm, $SP_{1X}=SP_{1Y}=SP_{2X}=SP_{2Y}=300$ nm, $W_{1X}=W_{1Y}=W_{2X}=W_{2Y}=600$ nm for the imaging structures, and $P_{3X}(1)=P_{3Y}(1)=P_{3X}(2)=P_{3Y}(2)=600$ nm (resulting in an effective pitch of 300 nm for zeroth order scatterometry structures 130A, 130B) and $P_{4X}(1)=P_{4Y}(1)=P_{4X}(2)=P_{4Y}(2)=1200$ nm (resulting in an effective pitch of 600 nm for first order scatterometry structures 130C). FIG. 3B schematically illustrates target 100 which is similar to the one illustrated in FIG. 3A but for the pitch values of imaging target structures 120A and 120B being $P_{1X}=P_{1Y}=P_{2X}=P_{2Y}=1200$ nm without further segmentation. FIG. 3C schematically illustrates target 100 which is similar to the one illustrated in FIG. 3A but for the pitch values of imaging target structures 120A and 120B being $P_{1X}=P_{1Y}=P_{2X}=P_{2Y}=600$ nm without further segmentation. In non-limiting examples, structure pitches may range between 1000 nm and 3000 nm for imaging targets and between 200 nm and 1000 nm for scatterometry targets, the latter further characterized by a predefined designed offset (not shown) between target structures (e.g., at different layers), which has much smaller dimensions than the structure elements (e.g., 16 nm) and is selected according to optical performance requirements.

Figure 4A:
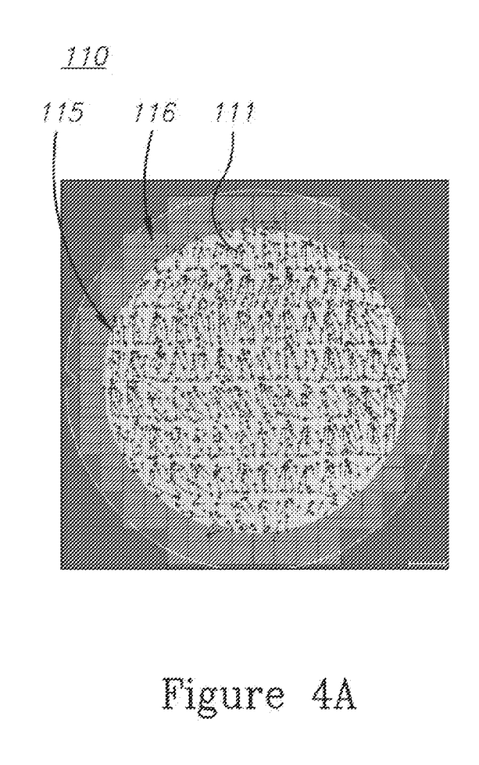
FIGS. 4A-4C are high level schematic illustrations for using the hybrid targets for different purposes at different regions on the wafer, according to some embodiments of the invention.
Figure 4B:
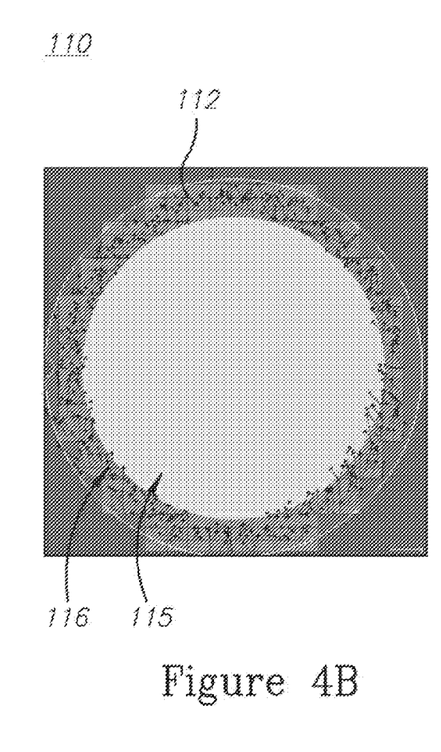
Figure 4C:
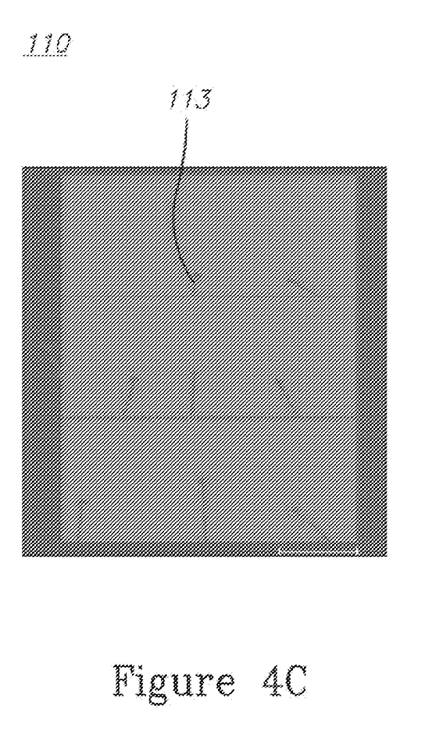

FIGS. 4A-4C are high level schematic illustrations for using targets 100 for different purposes at different regions on the wafer, according to some embodiments of the invention. FIGS. 4A-4C schematically illustrate results' images 110 for exemplary measurement wafer distributions.

FIGS. 4A and 4B illustrate a central wafer region 115 and a wafer periphery 116 in which overlays 111, 112 are measured using imaging techniques and scatterometry techniques (e.g., zeroth order SCOL), respectively, on the same hybrid targets configurations 100 all over the wafer. Central wafer region 115 may have, for example, a radius of 120 mm (or, in non-limiting examples, range between 100 mm and 150 mm). Central wafer region 115 may be select in different manners, e.g., according to the spatial distribution of process robustness of different target regions. Central wafer region 115 may be round due to radially-operating wafer processing steps such as etching and chemical-mechanical planarization (CMP) and/or edge-effected inaccuracies that occur at the wafer's periphery, but may also take other forms or comprise multiple regions in specific cases. FIG. 4C schematically illustrates measurements 110 of field correlation 113, i.e., overlay error vectors which visualize the overlay error signature at the field level. In certain embodiments, Process monitoring may be enhanced by measuring the distribution of overlays over the whole wafer or over specified regions of the wafer, and comparing results achieved by different measurement techniques.

Figure 5:
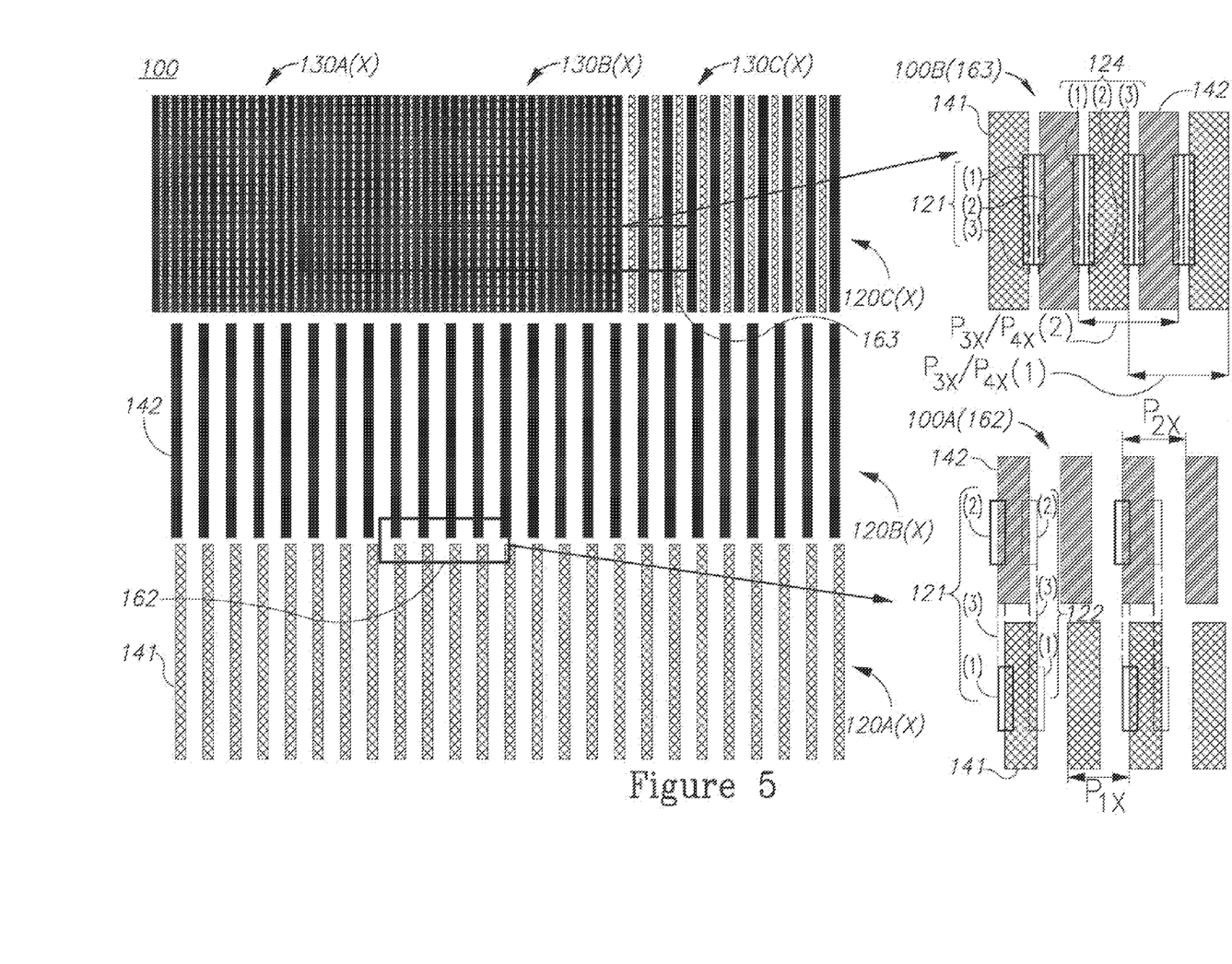
FIG. 5 is a high level schematic illustration of hybrid target used to conduct imaging measurements of target features using high resolution imaging, according to some embodiments of the invention.

FIG. 5 is a high level schematic illustration of target 100 used to conduct imaging measurements of target features using high resolution imaging, such as CD-SEM measurement, according to some embodiments of the invention. A exemplified on the bottom left quarter of target 100 illustrated in FIG. 1B, high resolution imaging such as scanning electron microscope (SEM) imaging may be conducted on details of target 100, such as details 100A defined by ROI 162 in the imaging region including illustrated imaging target structures 120A, 120B and/or details 100B defined by ROI 163 in the scatterometry region including any of illustrated scatterometry target structures 130A, 130B, 130C. In a non-limiting example, overlays (3) between layers 141, 142 may be measured using specified border areas of respective elements in these layers (1), (2). In the example, area pairs 121(1) and 121(2) may be used to measure overlay 121(3) and area pairs 122(1) and 122(2) may be used to measure overlay 122(3) in imaging region 100A and/or area pairs 123(1) and 123(2) may be used to measure overlay 123(3) and area pairs 124(1) and 124(2) may be used to measure overlay 124(3) in scatterometry region 100B.

In certain embodiments, hybrid targets 100 may be used to define and/or monitor any of the following: metrology measurement techniques, distribution of measurement types over the wafer, measurement recipes (algorithms and conditions) and their distributions over the wafer. In particular, the integration of structures which are measurable by various techniques provides maximal flexibility in optimizing and controlling the metrology strategy for the wafer and process as wholes.

Figure 6:
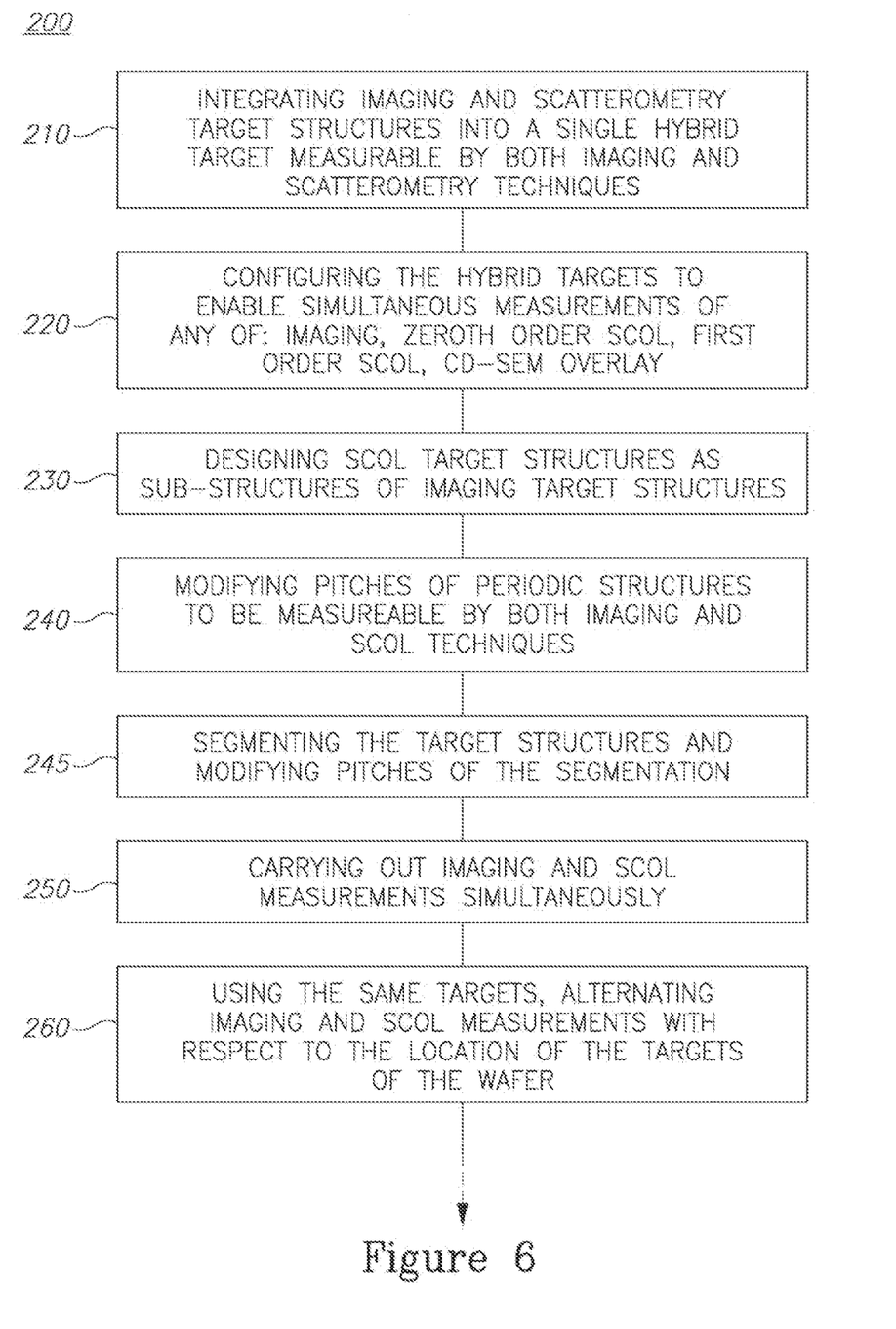
FIG. 6 is a high level schematic flowchart of a method, according to some embodiments of the invention.

FIG. 6 is a high level schematic flowchart of a method 200, according to some embodiments of the invention. Method 200 may comprise stages for designing and or producing targets 100, such as any of the following stages, irrespective of their order. Any of the designing and the configuring stages may be carried out by at least one computer processor. Certain embodiments comprise computer program products comprising a computer readable storage medium having computer readable program embodied therewith. The computer readable program may be configured to carry out stages of method 200. Also provided are design files which are produced according to stages of method 200. Certain embodiments comprise a computer program product comprising a computer readable storage medium having computer readable program embodied therewith. The computer readable program may be configured to carry out metrology measurements of targets 100 or any targets produced according to method 200, and/or according to respective measurement stages of method 200.

Method 200 may comprise integrating imaging and SCOL target structures into a single hybrid target measurable by both imaging and SCOL techniques (stage 210); configuring the hybrid targets to enable simultaneous measurements of any of: imaging, zeroth order SCOL, first order SCOL, CD-SEM overlay (stage 220); designing SCOL target structures as sub-structures of imaging target structures (stage 230); modifying pitches of periodic structures to be measureable by both imaging and SCOL techniques (stage 240) and/or segmenting the target structures and modifying pitches of the segmentation (stage 245); carrying out imaging and SCOL measurements of the hybrid target simultaneously (stage 250); using the same targets, alternating imaging and SCOL measurements with respect to the location of the targets of the wafer (stage 260); measuring process parameters using regions having different pitches on the hybrid targets (stage 270); and optimizing selection of metrology measurements and recipes over the wafer (stage 280).

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology target comprising at least one imaging target structure configured to be measurable by imaging and at least one scatterometry target structure configured to be measurable by scatterometry, the at least one imaging target structure comprising a portion bordering a first of the at least one scatterometry target structure, the portion comprising at least one periodic structure.

2. The metrology target of claim 1, wherein the portion comprises at least two periodic structures in different target layers.

3. The metrology target of claim 1, wherein the at least one scatterometry target structure comprises at least one periodic structure configured to provide zeroth order scatterometry overlay (SCOL) measurements and at least one periodic structure configured to provide first order scatterometry overlay (SCOL) measurements.

4. The metrology target of claim 1, wherein at least one of the at least one imaging target structure and the at least one scatterometry target structure is segmented.

5. A target design file of the metrology target of claim 1.

6. Imaging and scatterometry measurements of the metrology target of claim 1.

7. The metrology target of claim 1, wherein the first of the at least one scatterometry target structure is adjacent the at least one periodic structure.

8. A method comprising integrating imaging target structures and SCOL target structures into a single hybrid target measurable by both imaging and SCOL techniques such that a portion of the imaging target structure borders a first of the SCOL target structures and at least a second of the SCOL target structures forms a sub-structure of the portion.

9. The method of claim 8, further comprising configuring the hybrid target to enable simultaneous measurements of any of: imaging, zeroth order SCOL, first order SCOL, and CD-SEM overlay.

10. The method of claim 8, further comprising segmenting the target structures and modifying pitches of the segmented target structures to be measureable by both imaging and SCOL techniques.

11. The method of claim 8, further comprising carrying out imaging and SCOL measurements of the hybrid target simultaneously.

12. The method of claim 8, further comprising, using a same hybrid target type, alternating imaging and SCOL measurements with respect to a location of the target on a wafer.

13. The method of claim 8, further comprising measuring process parameters using regions having different pitches on the hybrid target.

14. The method of claim 13, wherein the process parameters are measured using scanning electron microscopy (SEM).

15. The method of claim 8, further comprising optimizing selection of metrology measurements and recipes over a wafer having the hybrid targets.

16. A computer program product comprising a computer readable storage medium having computer readable program embodied therewith, the computer readable program configured to carry out the method of claim 8.

17. A target design file, designed or produced according to the method of claim 8.

18. A multi-layer target designed, produced or measured according to the method of claim 8.

* * * * *